United States Patent
Hauk et al.

(10) Patent No.: US 7,612,233 B2
(45) Date of Patent: Nov. 3, 2009

(54) PRODUCTION OF SODIUM DIFORMATE

(75) Inventors: Alexander Hauk, Ludwigshafen (DE); Stefan Gropp, Speyer (DE); Robert Lenz, Neustadt/Weinstrasse Gimmeldingen (DE); Daniela Rieck, Alzey (DE); Jörg Heilek, Bammental (DE); Gerhard Laux, Frankenthal (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 11/913,122

(22) PCT Filed: May 2, 2006

(86) PCT No.: PCT/EP2006/004087

§ 371 (c)(1),
(2), (4) Date: Oct. 30, 2007

(87) PCT Pub. No.: WO2006/117187

PCT Pub. Date: Nov. 9, 2006

(65) Prior Publication Data

US 2008/0194874 A1     Aug. 14, 2008

(30) Foreign Application Priority Data

May 4, 2005  (DE) .................. 10 2005 020 890

(51) Int. Cl.
    *C07C 53/00* (2006.01)
(52) U.S. Cl. ...................................... 562/609
(58) Field of Classification Search ............ None
    See application file for complete search history.

(56) References Cited

U.S. PATENT DOCUMENTS

| 7,323,593 | B2 * | 1/2008 | Adami et al. | 562/609 |
| 2005/0256338 | A1 * | 11/2005 | Adami et al. | 562/609 |

FOREIGN PATENT DOCUMENTS

| DE | 424017 | 1/1926 |
| DE | 102005017089 | 10/2006 |
| EP | 0 824 511 | 2/1998 |
| WO | WO 96/35337 | 11/1996 |
| WO | WO 96/35657 | 11/1996 |
| WO | WO 2004/057977 | 7/2004 |

OTHER PUBLICATIONS

International Preliminary Report on Patentability for International Application No. PCT/EP2006/004087 dated Nov. 15, 2007.
Gmelins Handbuch der anorganischen Chemie, 8. Aufl., Nr. 21, S. 816-819, Verlag Chemie GmbH, Berlin, (1928).
Gmelins Handbuch der anorganischen Chemie, 8. Aufl., Nr. 22, S. 919-921, Verlag Chemie GmbH, Berlin, (1937).

\* cited by examiner

*Primary Examiner*—Karl J Puttlitz
(74) *Attorney, Agent, or Firm*—Connolly Bove Lodge & Hutz LLP (57) ABSTRACT

The calculation of the above balance shows that the division of stream (5) into the streams (5*a*) and (5*b*) used here leads to the fact that in the neutralization stage no excess sodium formate is produced, so that any ejection can be omitted. Furthermore, the water content of the stream (14) comprising sodium formate recirculated to the first crystallization stage in this case can be set to a very low value.

21 Claims, 5 Drawing Sheets

PRODUCTION OF SODIUM DIFORMATE

CROSS REFERENCE TO RELATED APPLICATIONS

This application is a National Phase of International Application No. PCT/EP2006/004087 filed on May 2, 2006, which in turn claims priority to Application No. 102005020890.8 filed in Germany on May 4, 2005; the entire contents of which are hereby incorporated by reference.

The present invention relates to a process for producing a solid sodium diformate preparation having a high content of formic acid.

DESCRIPTION

Acid formates have an antimicrobial activity and are used, for example, for preserving and for acidifying plant and animal materials, for instance grasses, agricultural products or meat, for treating biowastes or as an additive for animal nutrition.

In the field of animal nutrition, as sodium compounds, use is generally made either of mixtures of sodium diformate with trisodium hydrogenformate or the latter alone, see, e.g., WO 96/35337 and WO 04/57977. WO 96/35337, furthermore, reports on the use of sodium diformate, no specific instructions on the production of this compound being given.

Generally, for the use of hydrogenformates, a content of formate anions as high as possible as one of the active constituents is desirable. From the economic aspect, it is advantageous, in particular if this increased content of formate anions is accompanied by a formic acid fraction as high as possible, since this simultaneously offers the acidifying activity. From these aspects, the use of acid sodium formate is particularly expedient, since, in this case, compared with trisodium hydrogentetraformate, and also compared with acid potassium formate, in each case a higher theoretical content, both in formate ions and in formic acid, is present. Although both values are somewhat more expedient in the case of ammonium diformate, this is a very unstable compound, however.

Acid formates in solid form and their production have long been known as such, e.g. in Gmelins Handbuch der anorganischen Chemie [Gmelin's handbook of inorganic chemistry], 8th edition, Number 21, pages 816 to 819, Verlag Chemie GmbH, Berlin 1928, and also Number 22, pages 919 to 921, Verlag Chemie GmbH, Berlin 1937. The acid formates potassium diformate and sodium diformate are said in these citations to be obtainable in principle by dissolving potassium formate or sodium formate in formic acid and subsequent cooling. In addition to sodium diformate, the more stable crystal form trisodium hydrogentetraformate exists. However, reference is made to the fact that especially sodium diformate is accessible only with difficulty in crystalline dry form and, furthermore, is relatively unstable. The statements in Gmelin's handbook only permits the conclusion that the products described there were not pure sodium diformate.

German patent DE 424017 (of Jan. 14, 1926) teaches the production of acid sodium formates having various acid contents by introducing sodium formate into aqueous formic acid. The resultant crystals are obtained by cooling the solution to ambient temperature. Depending on the water content of the formic acid, in addition to trisodium hydrogenformate and mixtures of trisodium hydrogenformate with sodium diformate, sodium diformate is also reported to be accessible. The latter is said to be obtained by the process of DE 424017 when the formic acid used has a content of greater than 50%, e.g. 80%, as in Example 2. The inventors' own experiments, however, found that, under the conditions specified in DE 424017, sodium diformate cannot be obtained in pure crystalline form. Rather, in this procedure a mixture with trisodium hydrogenformate is obtained, the formic acid content of which is markedly below the theoretical value expected for pure sodium diformate of 40.36% by weight, based on the total dry weight.

EP 0 824 511 B1 describes a process for producing products which comprise disalts of formic acid. In this process, certain alkali metal or ammonium formates, hydroxides, (bi) carbonates, or ammonia are mixed at 40° C. to 100° C. with formic acid which has a content of at least 50%. The mixture is then cooled and the disalts are obtained by filtration. Although the production of acid potassium formate and also of mixtures of acid sodium formate with trisodium hydrogentetraformate is explained by way of example, the production of solid pure sodium diformate, in contrast, is not taught. For instance, this is because the temperatures and concentration limits specified for the (aqueous) potassium and sodium formate solutions to be used for the process only permit the production of potassium diformate, since (aqueous) solutions of sodium formate, owing to the lower solubility limit, compared with potassium formate, cannot be produced in the specified concentrations. Therefore, although potassium diformate is obtained, the sodium diformate is present exclusively in a mixture with trisodium hydrogentetraformate.

Furthermore, EP 0 824 511 B1 describes a processing method in which the mother liquor obtained after the crystallization is completely neutralized (pH=9 to 10) and is concentrated to a formate content of 70 to 80%, and in which the resultant formate solution is recirculated to the starting solution used for the crystallization. In order to be able to employ this process explained in EP 0 824 511 B1 by way of example on the basis of production of potassium diformate for producing sodium diformate, the sodium formate solution to be concentrated would have to be handled at comparatively high temperatures. For instance, a 70% strength by weight sodium formate solution is only obtainable at a temperature of about 135° C., and an 80% strength by weight sodium formate solution only at a temperature of 180° C. Such temperatures require high expenditure in the heating of the apparatuses used, for example piping and valves. If, after the concentration, an 80% strength by weight sodium formate solution is recirculated and mixed, e.g. with 85% strength by weight formic acid solution, the resultant solution, owing to its high water concentration, can only be crystallized industrially with high expenditure. The crystallization temperature of such a solution is below 20° C., so that generally a refrigeration unit requiring expenditure on energy costs and capital costs is necessary. Furthermore, in the neutralization of all of the mother liquor according to the process described in EP 0 824 511 B1, too much sodium formate is produced so that, when the overall balance is considered, an excess fraction must be ejected. This cannot be avoided even by using a more highly concentrated formic acid solution.

The previous German application DE 102005017089.7 describes for the first time a process for producing solid sodium diformate having a formic acid content of at least 35% by weight in pure stable and dry form.

Adequate stability of acid sodium formate in solid form is of particular importance not only with respect to handling and storage life, but also with respect to production. In particular, liberation occurring to a relatively great extent of the formic acid present in the acid sodium formate is undesirable, owing to its corrosive action.

In the field of animal nutrition, sodium diformate offers the advantage that the trace element sodium need not be added separately in the form of NaCl as otherwise customary, but already represents a sodium source as such. Owing to the high formic acid content in sodium diformate, e.g. compared with trisodium hydrogentetraformate, the content of sodium ions is limited. A low or limited content of cations, e.g. including potassium ions, is desirable to the extent that the latter in particular in the case of monogastric animals and especially in the case of poultry can lead to an increased liquid intake (increased drinking) and thus to dilution of the excreta of the animals, that is to say can develop diuretic activity.

The object underlying the present invention was to provide a process for producing a solid sodium diformate preparation which essentially consists of sodium diformate and avoids the above-described problems from the prior art. In particular, recycling the mother liquor to the production process should be enabled, without a significant fraction of sodium formate needing to be ejected. The inventive process should, furthermore, enable the production of a preparation which has a high formic acid content and in which the sodium diformate is present in high purity and also in comparatively stable and dry form, so that the process is applicable in the context of an industrial production, in particular at comparatively low temperatures.

This object has surprisingly been achieved by crystallizing out the target compound from a mixture of sodium formate having a more than one and a half times molar excess of formic acid while maintaining a molar ratio of formic acid to water of at least 1.1:1, recirculating a part of the mother liquor directly to the solution to be crystallized, and neutralizing the other part before the recirculation.

The present invention therefore firstly relates to a process for producing a solid sodium diformate preparation having a formic acid content of at least 35% by weight, based on the total weight of the sodium diformate preparation, in which, at elevated temperature from sodium formate and at least 74% strength by weight formic acid, an aqueous solution is produced which has a molar ratio of HCOOH:HCOONa of greater than 1.5:1 and a molar ratio of HCOOH:H$_2$O of at least 1.1:1, the aqueous solution is brought to crystallization, and the solid phase is separated off from the mother liquor,
(i) a subquantity (A) of the mother liquor being used in the production of the aqueous solution and
(ii) a subquantity (B) of the mother liquor being admixed with a sodium-containing base and the resultant mixture comprising sodium formate, if appropriate after ejecting a part of same, and if appropriate after concentrating same, likewise being used in the production of the aqueous solution;
and the subquantities (A) and (B) of the mother liquor totaling 100% by weight.

The starting materials sodium formate and formic acid used in the present invention are commercially available and can be used as such without pretreatment.

According to the invention, the mother liquor from the crystallization is used in the production of the aqueous solution. In this case, the subquantities (A) and (B) of the mother liquor are the only sodium formate source used in the inventive process. However, if mother liquor is not (yet) available, as is the case, e.g., before the process is carried out for the first time, e.g. technical-grade sodium formate can be used, for example at the start of a continuous processing method. Sodium formate produced in the production of polyols as waste product is also suitable in this case for use in the present invention. It is likewise possible to produce the sodium formate to be used, e.g. by reacting sodium hydroxide, carbonate or hydrogencarbonate with formic acid by reacting carbon monoxide with liquid sodium hydroxide or by reacting methyl formate with sodium hydroxide. In this variant, a procedure can be followed, e.g. in such a manner that solid NaOH or a concentrated aqueous solution thereof, if appropriate with cooling and/or stirring, is dissolved in preferably concentrated formic acid. The ratios of the starting materials can advantageously be directly selected in such a manner that the components formic acid, sodium formate and water are already present in the resultant mixture in the abovementioned molar ratios required. Otherwise, generally, neutralization of excess formic acid and/or reduction of the water content of the mixture by customary processes known to those skilled in the art, e.g. evaporation, extraction, distillation and the like, is required. Generally, a sodium formate is used, the HCOONa content of which is at least 97% by weight, based on the total weight of the sodium formate source used. Preferably, a sodium formate is used which comprises less than 0.1% by weight, and in particular less than 0.05% by weight, of potassium ions, in each case based on the total weight of the sodium formate source used. As soon as, after a first crystallization step (hereinafter also termed crystallization stage) mother liquor is available for use in the production of the aqueous solution, the subquantity (A) and the neutralized subquantity (B) of the mother liquor preferably serve as sole sodium formate source.

According to the invention, use is made of an aqueous formic acid solution having a formic acid content of at least 74% by weight, or a concentrated formic acid. A concentrated formic acid is taken to mean by those skilled in the art a formic acid solution having a formic acid content of 94% by weight or more, ie having a residual water content of less than 6% by weight, in each case based on the total weight of the formic acid solution. Aqueous formic acid is termed a solution of formic acid in water having a formic acid content of less than 94% by weight, based on the total weight of the aqueous formic acid solution. The aqueous formic acid solution used preferably has a concentration of at least 75% by weight, preferably at least 80% by weight, and particularly preferably at least 90% by weight. Very particularly preferably, use is made of concentrated formic acid having a formic acid content of at least 94% by weight. The concentration of the formic acid or formic acid solution preferably does not exceed 99% by weight, and is particularly preferably in the range form 80 to 99% by weight, and especially in the range form 94 to 98% by weight.

Preferably, use is made of concentrated or aqueous formic acid in an amount of at least 1.6 mol, in particular at least 1.8 mol, and especially at least 2.0 mol of HCOOH per mole of HCOONa. Preferably, the molar ratio of HCOOH:HCOONa used for producing the aqueous solution will be in the range form 1.6:1 to 3:1, and in particular in the range from 1.8:1 to 2.5:1.

Preferably, the molar ratio of HCOOH:H$_2$O used for producing the aqueous solution will be at least 1.5:1, and particularly preferably at least 1.8:1, very particularly preferably it is in the range from 1.5:1 to 10:1, and in particular in the range from 1.8:1 to 6.1:1.

According to the invention, the aqueous solution is produced at elevated temperature. This is generally taken to mean temperatures of at least 30° C., in particular at least 40° C., and especially at least 50° C., with, generally, 100° C., in particular 80° C., and especially 70° C., not being exceeded. Such an aqueous solution can be produced using customary procedures known to those skilled in the art, e.g. by mixing, agitating or dissolving with use of elevated temperature, or by combined use of these methods. The sequence of use of the starting materials is of subsidiary importance. This applies not only to a first time the process is carried out, in which mother liquor is not yet available for recirculation, but also in the case of recirculation of the substreams (A) and (B) of the mother liquor. Advantageously, the mixing is performed in such a manner that a homogeneous liquid mixture of the starting materials is obtained in the molar ratio to be maintained. If this homogeneous liquid mixture is not already the aqueous solution, for instance because not all components are present in completely dissolved form, the homogeneous liquid mixture is converted to the aqueous solution by increasing the temperature, preferably with stirring.

To carry out the inventive process, generally a procedure is followed in such a manner that an aqueous or concentrated, preferably concentrated, solution of formic acid is present as initial charge. To this formic acid solution is added the sodium formate in solid form or in the form of an aqueous solution or suspension, if appropriate together with further formic acid. Alternatively, it is also possible to combine the starting materials in reverse order. If, in the latter case, solid sodium formate is used and charged first, advantageously, then, by adding a part of the formic acid to be used or a part of the subquantity (A) of the mother liquor, a stirrable or pumpable mixture is produced to which the remaining subquantity of the formic acid is added.

The subquantity (A) of the mother liquor from step (i) is used, preferably as a solution in non-prepared form, for producing the aqueous solution. Of course, it can also be stored in the interim and used as required at a later timepoint for producing the aqueous solution. In this case, the subquantity (A) is used, e.g. as solution or suspension, preferably as solution.

The mixture resulting from step (ii) after neutralization of the subquantity (B) of the mother liquor is generally used as aqueous suspension or as solid in the production of the aqueous solution. If appropriate, before the use for producing the aqueous solution, a part of the mixture is ejected. The mixture, before use, is preferably partly or completely evaporated. The mixture, in the production of the aqueous solution, can be added, in each case in portions, e.g. in 2, 3, 4 or more individual portions, which are added to the reaction mixture at a predetermined time interval from one another, or can be added continuously, ie at constant, decreasing or increasing rate. During the addition, generally a temperature increase occurs, so that, if appropriate additional heating is not required. Customarily, the temperature of the mixture is set, e.g. by adjusting the addition rate and/or cooling or heating the mixture and/or the solution added, in such a manner that in the mixture a temperature in the range from 30° C. to 80° C., and in particular from 40° C. to 70° C., is maintained. Preferably, the temperature of the mixture is not above 65° C. It is critical to the invention that the crystallization takes place from an aqueous solution. It is possible, as explained in more detail hereinafter, that this is admixed, or for this to be admixed, with seed crystals even before the start of the crystallization.

During the addition of the sodium formate, the solution or suspension is advantageously agitated, e.g. stirred. The agitation is continued after completion of the addition at least until an aqueous solution is obtained, generally until the end or termination of the crystallization.

According to the invention, the starting materials can be mixed in all apparatuses customarily used for the purpose of producing a homogeneous liquid mixture, such as reactors, kettles, flasks, etc., in particular in stirred vessels, especially those having internal heat exchangers. These are known to those skilled in the art. To avoid corrosion effects, e.g. in reactors or kettles made of steel, it is advantageous if the surfaces and walls coming into contact with formic acid are coated with an acid-resistant protective coat, e.g. of Teflon®, or are lined with specially acid-resistant high-alloy steels.

The aqueous solution, preferably with continued stirring, is then brought to crystallization. This can be achieved, e.g. by partial evaporation or by cooling, preferably by cooling. If the crystallization is achieved or initiated or accelerated by controlled evaporation of the aqueous phase, preferably under vacuum, it must be ensured that the molar ratios of the components in the solution are within the above-specified ranges at the start of the crystallization. If the crystallization is achieved by cooling, this preferably proceeds slowly, advantageously over a period of one to a plurality of hours, e.g. up to 12 h, in particular form 3 to 10 h, and especially from 4 to 8 h. In this case the sodium diformate crystallizes out. It has proved to be advantageous if the cooling proceeds at a cooling rate in the range from about 2 to about 20 K/h, e.g. about 5 to 15 K/h. To achieve thorough crystallization of the target compound, it is advantageous to cool the aqueous solution in said period to a temperature of below 20° C., e.g. about 15° C. or lower, or 10° C. or lower. Generally, in this case, the temperature does not fall below a temperature of 0° C., and in particular 5° C.

It has proved to be advantageous, after initiation of crystal formation, to dissolve the crystal nuclei or small crystals first formed by heating, e.g. to a temperature of a maximum of 65° C., in particular in the range from 25° C. to 50° C., and then to start the crystallization process again by further, if appropriate slow, cooling. In this further cooling, the rate is customarily in the range from about 0.5 to about 20 K/h, e.g. at about 1 to 15 K/h, in particular at about 2 to 15 K/h, especially at about 5 to 10 K/h, and preferably at a maximum of 25 K/h. The crystallization temperature is in the ranges mentioned above.

In addition, it can be advantageous to add, to the aqueous solution, preexisting crystals of sodium diformate, e.g. produced in advance by the inventive process, to promote the crystallization process, ie for the purpose of what is termed "seeding". Such crystals can be added in dry or moist form, suspended in a liquid, e.g. aqueous or formic acid, phase, or a combination of these forms. The addition is usually performed above a temperature which leads to crystal formation, but below a temperature at which a homogeneous solution is present. The temperature of the reaction mixture therefore does not generally exceed 65° C. on addition of crystals, and is preferably in the range from 25 to 50° C. The crystallization process can then take place, as described above, at a cooling rate in the range of about 0.5 to about 20 K/h, e.g. about 1 to 15 K/h, in particular about 2 to 15 K/h, and especially about 5 to 10 K/h. The crystallization temperature is in the above-specified ranges.

Subsequent to the crystallization, the resultant solid product is separated off from the mother liquor. The solid phase can be separated off from the mother liquor by processes which are customary for this and known to those skilled in the art, e.g. filtration or centrifugation, preferably by centrifugation, in particular with use of pusher-type or peeler centrifuges. The sodium diformate preparation thus produced generally further comprises small amounts of formic acid, water and/or sodium formate. The formic acid content in this still-moist sodium diformate preparation is customarily greater than 40.3% by weight, and in particular in the range from 40.7 to 42.5% by weight, based on the total weight of the moist preparation.

The moist product is then dried by customary drying processes, e.g. under vacuum and/or moderate heating. Driers and drying processes which are usable for this are known to those skilled in the art and are described, e.g. in K. Kröll, Trockner und Trocknungsverfahren [Driers and drying processes], 2nd edition, Springer Verlag, Berlin 1978. In particular, use can be made of, e.g., contact driers, fluidized-bed driers, spray driers and jet driers. The relatively high volatility of the formic acid present in the product and also the limited temperature stability of the product must be taken into account. During the drying, the product temperature generally does not exceed 65° C., and in particular 50° C. The water content remaining in the product after drying (residual water content) is generally no greater than 0.5% by weight, and is customarily in the range from about 0.5 to 0.01% by weight, preferably a maximum of 0.3% by weight, particularly preferably a maximum of 0.2% by weight, and very particularly preferably a maximum of 0.1% by weight, based on the total weight, determined by oxidimetric titration by Karl Fischer (e.g. described in Wiland, Wasserbestimmung durch Karl-Fischer-Titration [Water determination by Karl-Fischer titration], Darmstadt, GIT, 1985).

Here and hereinafter, the expression total weight of the sodium diformate preparation is used synonymously with the expression total dry weight. The total dry weight is taken to mean the weight of the sodium diformate preparation which is yielded by drying the product below its decomposition temperature, e.g. by drying over a period of 1 h at a temperature of 35° C. and a pressure of 50 mbar.

To carry out the inventive process it is advantageous to achieve as high a yield as possible in the crystallization of the sodium diformate, because as a result the internal mass streams can be minimized. As a result, the apparatus requirements can be reduced, in that, e.g., the apparatuses used can be dimensioned to be smaller.

The mother liquor separated off subsequent to the crystallization is according to the invention divided into two subquantities (A) and (B). The subquantity (A) is, together with the formic acid solution and the subquantity (B) worked up according to step (ii), recirculated to the crystallization stage, if appropriate after partial or complete mixing of said mass streams. In this case the subquantities (A) and (B) can be stored temporarily in customary vessels such as tanks or kettles, whereby the metering can be controlled as required. The weight ratio of subquantity (A) to subquantity (B) of the mother liquor is preferably in the range from 20:1 to 1:10, still more preferably in the range from 10:1 to 1:5, particularly preferably in the range form 8:1 to 1:2, and very particularly preferably in the range from 5:1 to 1:1. The volumetric streams to be set can be established from the equivalent molar concentration of formic acid in the subquantities (A) and (B).

The subquantity (B) is fed to a neutralization stage in which a partial or complete neutralization takes place. Sodium-comprising bases suitable for this are sodium hydroxide, sodium carbonate, sodium hydrogencarbonate, sodium $C_1$-$C_6$-alkanolates, such as sodium methoxide, ethoxide, propoxide, butoxide, pentoxide and hexoxide, and mixtures thereof. Preferably, the base is selected from sodium hydroxide, sodium carbonate and mixtures thereof. The bases can be used, e.g. in the form of an aqueous solution. Preferably, the subquantity (B) is admixed with a sodium hydroxide- and/or sodium carbonate-comprising solution, e.g. a 50% strength by weight sodium hydroxide solution, a 20 to 30% strength by weight sodium carbonate solution or a mixture thereof. Preferably, the subquantity (B) is essentially completely neutralized. Essentially complete neutralization here means that the amount of the base used is equivalent at least to the formic acid present in the subquantity (B) and to this extent theoretically sufficient for complete neutralization.

From the mixture comprising sodium formate resulting from the neutralization, if appropriate a part is taken and this is ejected. This can be necessary to remove an excess of sodium formate produced in the neutralization on consideration of the overall balance. For the inventive process it is preferred to keep the fraction of sodium formate to be ejected as low as possible in order to enable optimum process conditions and product yield. Generally, the amount ejected is at most 20% by weight, in particular at most 10% by weight, and especially at most 5% by weight, of the mixture comprising sodium formate, based on the total weight of the mixture. Preferably, only a part of the mixture is ejected such that the amount of sodium formate present in the remaining part of the mixture, together with the amount of sodium formate present in the subquantity (A) of the mother liquor yields the total amount of sodium formate used for producing the aqueous solution (ie the use of additional sodium formate is not required).

The non-taken part of the mixture comprising sodium formate resulting from the neutralization is fed to a concentration stage, preferably an evaporation stage. In this, a part of the water present in the mixture is discharged, preferably by evaporation. The fraction of the water discharged in this case depends on in what form the sodium formate present in the mixture is to be recirculated to the crystallization stage. This can be performed, e.g. in the form of a solution, suspension or as solid. Preferably, the recirculation is performed as pumpable suspension or as solid which, if appropriate, still has fractions of residual moisture. The mixture which comprises sodium formate and which is withdrawn from the concentration stage and recirculated generally has a sodium formate content of at least 50% by weight, in particular at least 60% by weight, especially in the range from 50 to 100% by weight, and highly especially in the range from 70 to 90%, in each case based on the total weight of the recirculated mixture. The water content of the mixture is preferably at most 25% by weight, and particularly preferably at most 15% by weight, in each case based on the total weight of the mixture. The mixture comprising sodium formate which is obtained and/or worked up is recirculated to the crystallization stage.

The water content can also be decreased by means of a second crystallization stage in which a second solid phase and a second mother liquor are obtained, and a second concentration stage in which the second solid phase is separated off from the second mother liquor. In this case, the second solid phase is sodium formate. Its crystallization conditions are known to those skilled in the art and are described, e.g. in Zagidullin, S. K., et al., "Investigation of Supersaturations in the Sodium Formate—Water System to Optimize Crystallization", Russian Journal of Applied Chemistry, Vol. 69 (1996), 5, 669-672. For example, an evaporative crystallization or a cooling crystallization can be carried out by means of wall cooling or evaporative cooling. It must be noted that at low temperatures, e.g. at below 30° C., or below 20° C., hydrate forms of the sodium formate which have more than one $H_2O$ molecule bound as crystal water per sodium formate unit can crystallize out. This is generally undesirable and is therefore to be avoided, in particular by crystallization at relatively high temperatures.

The second solid phase which results in this case can have a low water content of less than 15% by weight, in particular less than 10% by weight, and especially less than 5% by weight. An especial advantage of this low water content is that the sodium diformate can be crystallized at low water contents, e.g. at less than 10% by weight, based on the aqueous solution which is brought to crystallization. As a result, higher crystallization temperatures and also higher yields at a fixed end temperature can be achieved.

The inventive process can be carried out particularly advantageously if the molar amount of formic acid present in the subquantity (B) is roughly equivalent to the molar amount of sodium diformate ejected with the product stream (and if appropriate sodium formate which in particular can adhere to the product owing to residual moisture), or is insignificantly above this, ie if a molar ratio of these components of about 1:1 is present. This is because in this case it is possible in a simple manner to obtain all of the sodium formate to be used via the recirculated mass streams, without ejection of surplus sodium formate being necessary. A part of the sodium formate in this case is again fed into the process via the recirculation of the mother liquor. The remaining part can in this case be completely effected by recirculating the neutralized and/or concentrated subquantity (B) of the mother liquor. To carry out this process variant, generally the ratio of subquantity (A) to subquantity (B) of the mother liquor is set in such a manner that the molar ratio of HCOOH in subquantity (B) of the mother liquor to the total amount of the sodium diformate present in the resultant solid phase and sodium formate present if appropriate, before a subsequent drying, if appropriate, of the solid phase is at most 1.2:1, preferably at most 1.1:1, and particularly preferably at most 1.05:1.

In a preferred embodiment, a procedure is followed in such a way that a) a stream (1) of formic acid having a formic acid content of at least 74% by weight is prepared;
b) the stream (1) from step a) having two streams (5a) and (10) comprising the sodium formate is fed to a crystallization stage, wherein, if appropriate with temperature elevation, the aqueous solution which has a molar ratio of HCOOH:Na[HCOO] of greater than 1.5:1 and a molar ratio of HCOOH:H$_2$O of at least 1.1:1 is produced;
c) in the crystallization stage the aqueous solution from step b) is brought to crystallization to produce a stream (3) having the solid phase and the mother liquor;
d) the stream (3) from step c) is fed to a separation stage in which the solid phase is separated off from the mother liquor, a stream (4) comprising the sodium diformate and a stream (5) comprising the mother liquor being produced;
e) the stream (5) from step d) is divided into two substreams (5a) and (5b);
f) the stream (5a) from step e) is recirculated as subquantity (A) to step b);
g) the stream (5b) from step e) is fed to a neutralization stage as subquantity (B) together with a stream (6) comprising the sodium-containing base, resulting in the mixture comprising sodium formate; and
h) the comprising sodium formate mixture from step g), if appropriate after taking off a part of same in the form of stream (7a), is fed as stream (7) to a concentration stage in which a part of the water present in the stream (7) is discharged as stream (9), the stream (10) comprising sodium formate being produced, which is recirculated to the step b).

Figure 2:
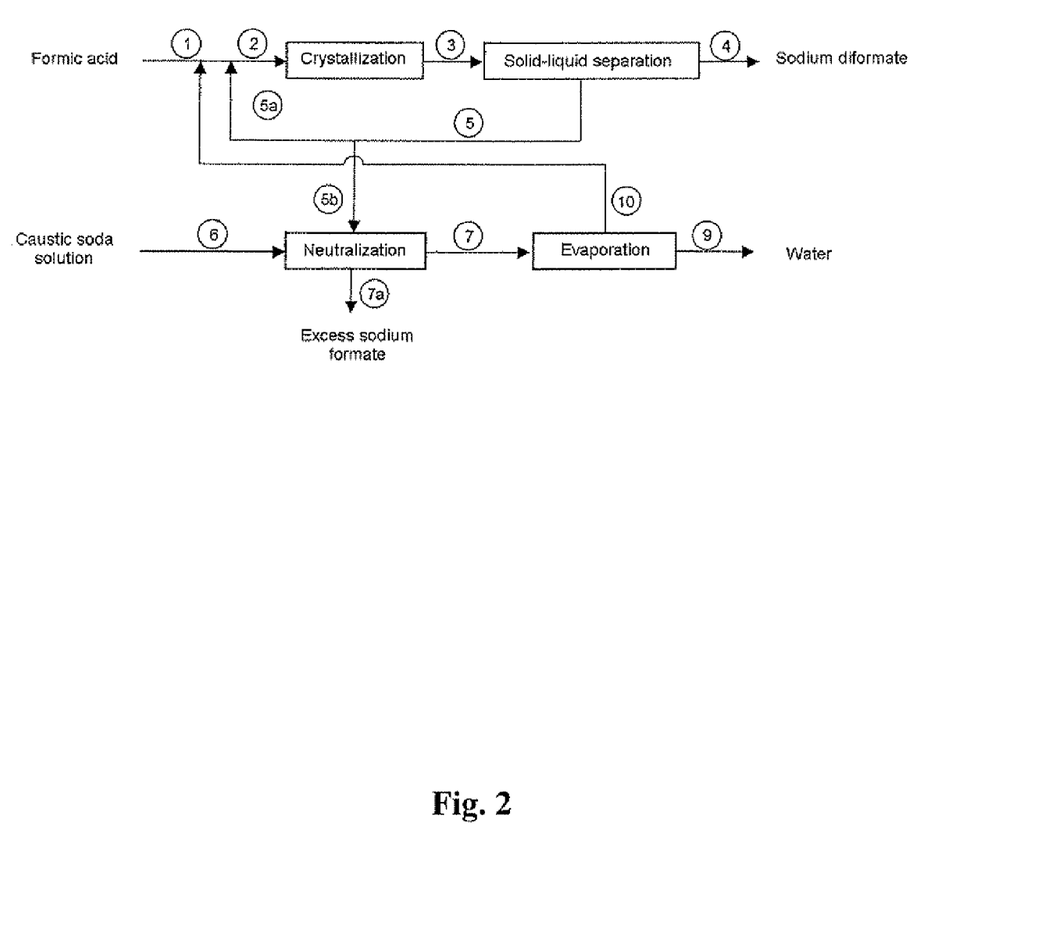
FIG. 2 shows a diagrammatic representation of a process variant of the inventive process. The stream (5b) is neutralized, concentrated by evaporation and recirculated to the crystallization stage.

A diagram of the process corresponding to this preferred embodiment is shown in the accompanying FIG. 2. The streams (5a) and (10) can be mixed with the stream (1) in step b) before or after feeding to the crystallization stage, e.g. before the feed in such a manner that first stream (10) and then stream (5a) is fed to the stream (1). Of course, the streams (5a) and (10) can also be mixed with one another before being combined with the stream (1) or before feed to the crystallization stage.

Customarily in the case of this embodiment, in step d), the stream (5) essentially comprises formic acid in the range from 35 to 80% by weight, particularly preferably in the range from 40 to 75% by weight; sodium formate in the range form 20 to 45% by weight, particularly preferably in the range form 20 to 40% by weight; and water in the range from 0 to 30% by weight, particularly preferably in the range from 5 to 25% by weight; in each case based on the total weight of the stream (5). In step g), as stream (6), use is preferably made of an aqueous solution comprising sodium hydroxide, sodium carbonate and/or sodium hydrogencarbonate solution. Particular preference is given to an aqueous caustic soda solution having an NaOH content in the range form 10 to 60% by weight, and preferably in the range from 20 to 55% by weight, in each case based on the total weight of the aqueous caustic soda solution. The stream (10) from step h) customarily essentially comprises sodium formate in the range from 50 to 100% by weight, preferably in the range from 55 to 95% by weight, and particularly preferably in the range from 70 to 90% by weight; and water in the range from 0 to 50% by weight, preferably in the range form 5 to 45% by weight, and particularly preferably in the range from 10 to 30% by weight, in each case based on the total weight of the stream (10).

The expression "essentially" means here that no significant fractions of other materials are present in the respective stream. For example, in stream (5), low amounts of small sodium diformate crystals can be present which have not been conjointly separated off in the phase separation in the separation stage, or which have been newly formed after separation. Generally, the fraction of other materials in the streams (5) and (10), however, is no greater than 5% by weight, and in particular no greater than 3% by weight.

In a further preferred embodiment, the sodium formate-comprising stream (10) from step h), before the recirculation to step b), is fed to a second crystallization stage and a second separation stage. In detail, a procedure is followed in such a way that k) the sodium formate-comprising stream (10) from step h), before it is recirculated to step b) is fed to a second crystallization stage and is brought herein to crystallization, producing a second solid phase and a second mother liquor;
l) the second solid phase and second mother liquor obtained from step k) is fed in the form of a stream (12) to a separation stage in which the second solid phase is separated off from the second mother liquor, producing a stream (13) comprising the second mother liquor and a stream (14) comprising sodium formate;
m) the sodium formate-comprising stream (14) from step l) is recirculated to the step b) and used herein as stream (10); and
n) the mother liquor-comprising stream (13) from step l)
  n1) is recirculated to the step h) and herein is fed together with the stream (7) to the concentration stage of the step h);
  n2) is recirculated to the step k) and herein is fed together with the stream (10) to the second crystallization stage;
  n3) is divided into the substreams (13a) and (13b), the substream (13a) is recirculated to the step h) and herein is fed together with the stream (7) to the concentration stage of the step h) and the substream (13b) is recirculated to the step k) and herein is fed together with the stream (10) to the second crystallization stage; and/or
  n4) is in part taken off and ejected.

Figure 3:
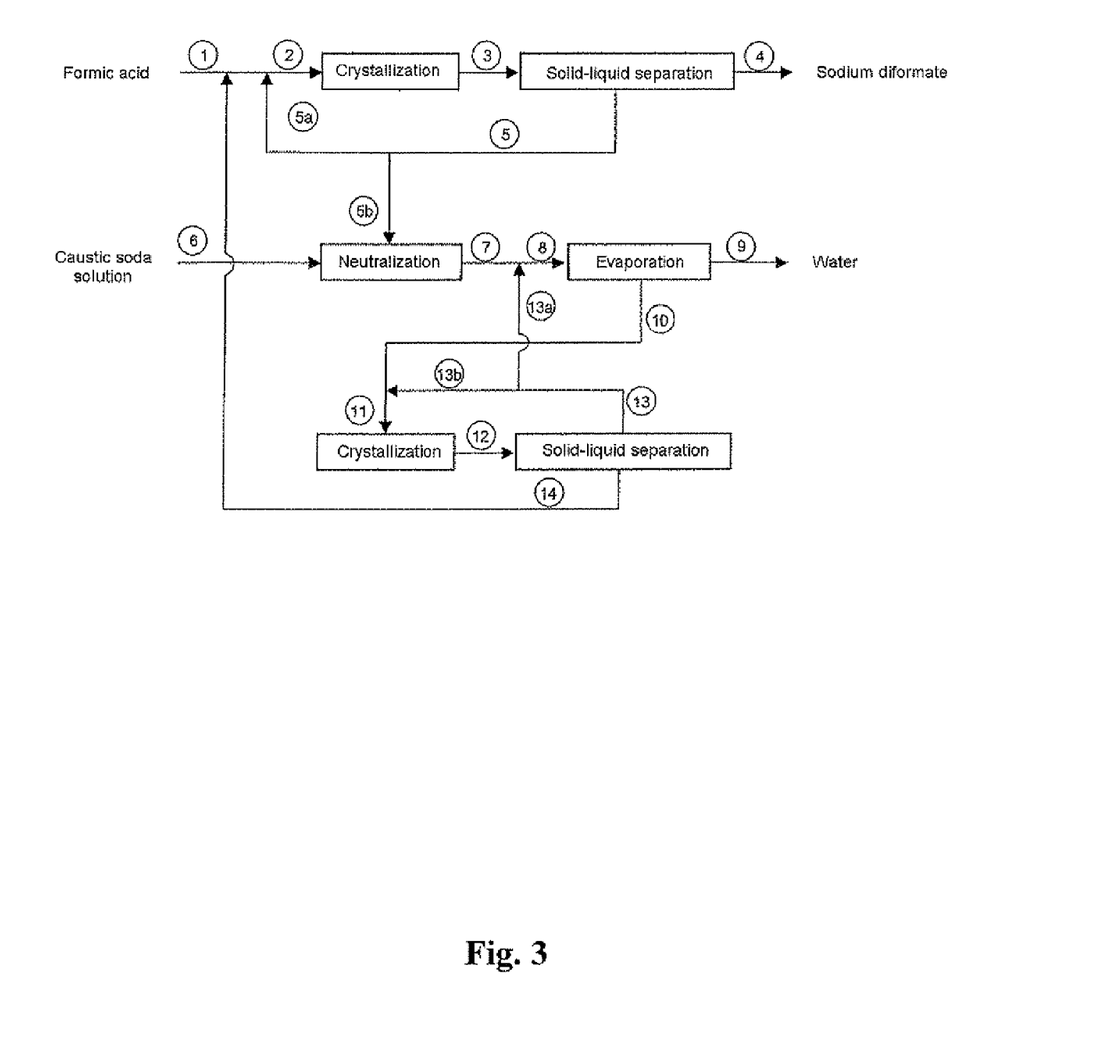
Figure 4:
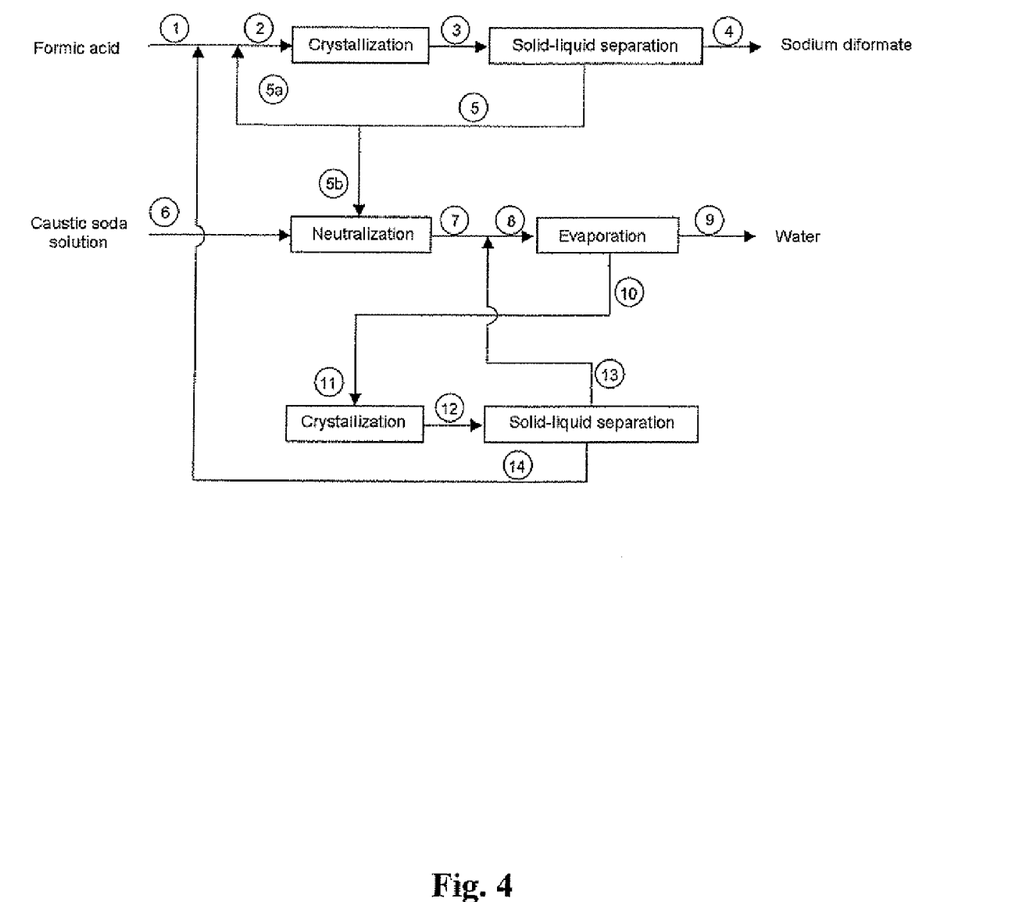
Figure 5:
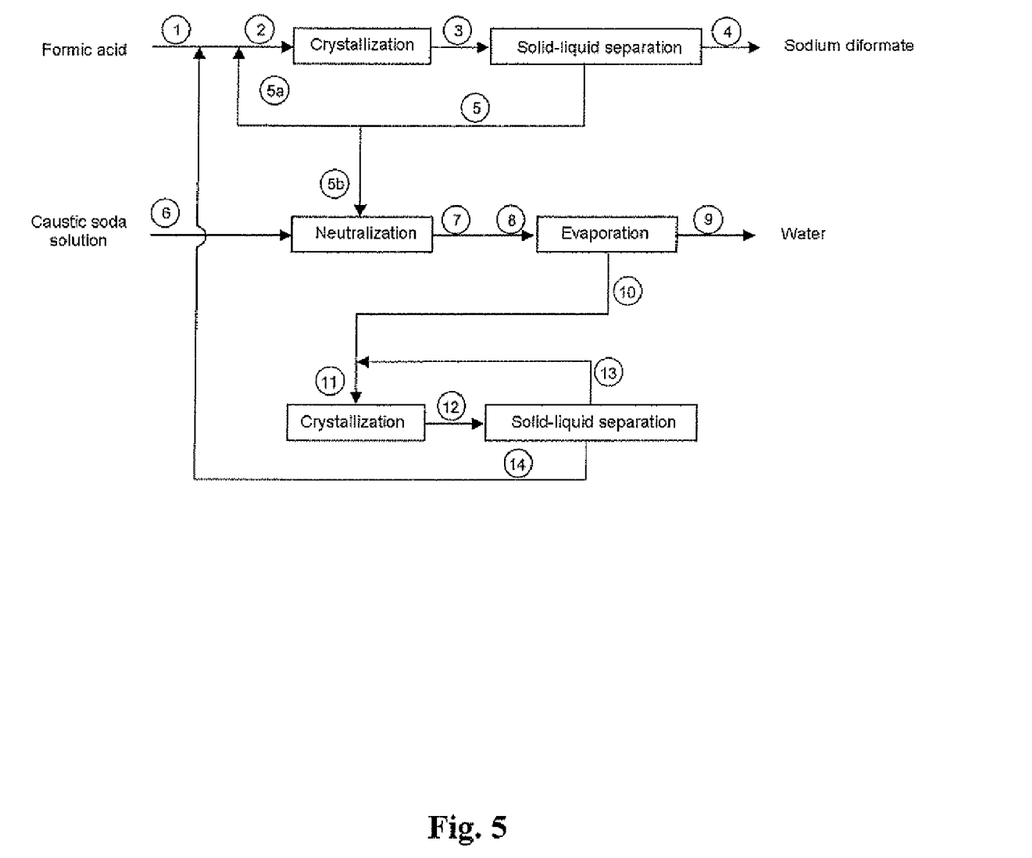

A diagram of the process equivalent to this preferred embodiment is reproduced in the accompanying FIGS. 3, 4 and 5.

Customarily in this embodiment, the stream (13) from step l) comprising the mother liquor essentially comprises water in the range from 20 to 60% by weight, preferably in the range from 25 to 55% by weight, and particularly preferably in the range from 30 to 50% by weight; and sodium formate in the range from 40 to 80% by weight, preferably in the range from 45 to 75% by weight, and particularly preferably in the range from 50 to 70% by weight, in each case based on the total weight of the stream (13). The stream (13) from step l) comprising the mother liquor is recirculated preferably either according to step n1) to step h), or according to step n2) to step k). In step h), the recirculated stream (13) can be combined with the stream (7) producing a stream (8); the stream (8) is then fed to the concentration stage of step h). Of course, the stream (7) and the recirculated stream (13) can also be fed separately to the concentration stage. In the step k), the recirculated stream (13) can be combined with the stream (10) to produce a stream (11); the stream (11) is then fed to the second crystallization stage of step k). Of course, the stream (10) and the recirculated stream (13) can also be fed separately to the second crystallization stage. If appropriate, the stream (13) from step l) can be taken off in part according to step n4) and this substream which is taken off is ejected. In this case, generally, at most 30% by weight, in particular at most 20% by weight, and especially at most 10% by weight, of the stream (13), based on the total weight of the stream (13), is taken off and ejected. Generally, the stream (13) from step l) comprising the mother liquor is ejected in part only to the extent as is required, e.g., for regulating the material balance, in particular the water content. Preferably, in step n), no part of stream (13) is taken off according to step n4). Customarily, the sodium formate-comprising stream (14) from step l) essentially comprises sodium formate in the range from 75 to 100% by weight, in particular in the range from 90 to 99% by weight, and especially in the range from 95 to 98% by weight; and water in the range from 0 to 25% by weight, in particular in the range from 1 to 10% by weight, and especially in the range from 2 to 5% by weight, in each case based on the total weight of stream (14).

The expression "essentially" here means that no significant fractions of other substances are present in the respective stream. Generally, the fraction of other substances in the streams (13) and (14) will be no more than 5% by weight, and in particular no more than 3% by weight.

The inventive process can be carried out continuously, semicontinuously, or batchwise.

The sodium diformate preparation is obtained by the inventive process in high purity and therefore, after drying, has a high content of formic acid, generally at least 35% by weight, frequently at least 36% by weight, in particular at least 37% by weight, especially at least 38% by weight, very especially at least 39% by weight, and more especially at least 40% by weight, in each case based on the total weight of the sodium diformate preparation. Generally, the content of formic acid in the inventively obtained sodium diformate preparation is no more than 41% by weight, and in particular no more than 40.5% by weight, in each case based on the total weight. Especially, the content is in the range from 38 to 41% by weight, very especially in the range from 39 to 40.5% by weight, and more especially in the range from 40 to 40.3% by weight, in each case based on the total weight of the obtainable sodium diformate preparation. The formic acid content in the dry product can be determined in a conventional manner, e.g. by titration of the formic acid with a base. Naturally, likewise a high content of formate anions is present in the dry product.

The inventively obtained sodium diformate preparation is typically obtained in crystalline form. It is assumed that the preparation corresponds essentially or completely to the formula HCOONa.HCOOH (sodium diformate) which, however, is not to be understood as a limitation of the invention. Rather, it is essential to the invention that the preparation has sodium formate and formic acid in associated crystalline form. The inventively obtained crystalline modification of the sodium diformate may be identified, for example, by x-ray wide-angle scattering. Unwanted modifications, e.g. trisodium hydrogentetraformate, can likewise be detected qualitatively by the same method. The molar ratio of the components sodium formate and formic acid in the preparation is customarily in the range from 0.9:1 to 1.1:1, in particular in the range from 0.95:1 to 1.05:1, and corresponds especially to about 1:1. The fraction of sodium diformate in the preparation is customarily at least 97% by weight, in particular at least 98% by weight, and especially at least 99% by weight, in each case based on the total weight of the preparation. As further constituents, the preparation, owing to residual moisture or crystalline residual moisture, can comprise generally up to 1.5% by weight of formic acid, up to 1.5% by weight of sodium formate and/or up to 0.5% by weight of water, in each case based on the total weight of the preparation. At about 65° C., by means of DSC (differential scanning calorimetry), a phase transition point can be observed. The preparation is distinguished by a comparatively low hygroscopicity, in particular compared with trisodium hydrogentetraformate. Furthermore, the inventively obtained sodium diformate preparation is sufficiently stable to ensure problem-free handling and (further) processing. In addition, the content of potassium ions of the preparation obtained is generally at most 1000 ppm, and in particular at most 500 ppm, in each case based on the total weight. The chloride content owing to the preparation in the inventively obtained sodium diformate preparation is generally less than 1500 ppm, and in particular less than 1000 ppm, in each case based on the total weight.

The inventive process for producing a solid, dry sodium diformate preparation in crystalline stable form makes it possible to apply the preparation conditions to an industrial scale. It is distinguished in particular by the fact that an efficient way for ejecting water is realized. By this means, especially the water content of the aqueous solution to be crystallized can be kept low, which is accompanied by the abovementioned advantages.

The resultant solid product can be comminuted before and/or after the drying step, e.g. by means of mortars, cutters, punch presses and rolling mills, agglomerated, e.g. by means of mixers, and/or compacted, e.g. by means of presses and compactors. The apparatuses used for such a comminution are known to those skilled in the art.

Depending on the desired purpose of use, the inventively produced sodium diformate preparation can be further processed, in particular powders of defined particle sizes can be produced, the particles produced can be covered with coatings and/or mixtures with other additives can be prepared. As examples of coatings or coating materials which may be mentioned are oils such as soybean oil, fats and fatty acids such as palmitic or stearic acid, or polymer coatings, e.g. made of polyalkylenes and derivatives thereof. Customary additives are, in particular, flow aids such as silica etc. Suitable processes for coating and also the additives coming into consideration are thoroughly known to those skilled in the art in the respective field, see, e.g. DE 102 31 891 A1.

According to the invention the sodium diformate preparation produced is in solid form, in particular as crystal powder or as granules or compactate. Depending on the applicationorientated requirements, the powders, granules or compactates have a mean particle size in the range from 1 μm to 10 000 μm, in particular from 10 μm to 5000 μm, and especially from 100 μm to 2500 μm.

The inventively produced solid sodium diformate preparation and formulations and compositions comprising this are suitable for use in feeds for animals (animal feeds), in particular as additive to animal feed in the form of feed additives and especially as additive to premixes for animal feeds. Premixes are mixtures which generally comprise minerals, vitamins, amino acid, trace elements and also if appropriate enzymes. Animals feeds and feed additives which comprise the inventively prepared solid sodium diformate preparation are particularly suitable for monogastric animals such as hogs, especially piglets, breeding sows and fattening hogs, and also poultry, especially broilers, laying hens, turkeys, ducks, geese, quails, pheasants and ostriches.

Depending on the remaining substances or additives present in the feed or feed additive, the content of the inventively prepared solid sodium diformate preparation in the feed or feed additive can vary greatly. In the case of feed additives, the content furthermore depends on the type of the formulation, e.g. on the addition of additives such as desiccants, on a possible coating and on the residual moisture content. Customarily, the content of inventively produced solid sodium diformate preparation in the feed additive is, e.g. in the range from 0.1 to 99.5% by weight, in particular from 0.5 to 75% by weight, and especially from 1 to 50% by weight, based on the total dry weight of the feed additive. The inventively produced solid sodium diformate preparation is also suitable for use in a premix and can in this case be used in the customary amounts, e.g. admixed.

In particular in the case of use in animal feed and in feed additives for poultry, a small content of potassium ions is advantageous, since potassium in this case can develop a diuretic action. The use of the inventively produced sodium diformate preparation for the abovementioned purpose thus provides an acidic sodium and formate source, without necessarily the fraction of potassium ions being increased. For instance, a solid feed additive can be formulated which comprises the inventively prepared solid sodium diformate preparation and is essentially free from potassium ions. In this case essentially free from potassium ions means that the content of potassium ions is at most 1000 ppm, and in particular at most 500 ppm, in each case based on the weight of the feed additive.

Animal feeds are composed in such a way that the corresponding requirement for nutrients are optimally covered for the respective animal species. Generally, plant feed components such as corn, wheat or barley meal, whole soybean meal, soybean extraction meal, linseed extraction meal, rapeseed extraction meal, green meal or pea meal are selected as crude protein sources. To ensure an appropriate energy content of the feed, soybean oil or other animal or vegetable fats are added. Since the plant protein sources comprise some essential amino acids only in an insufficient amount, feeds are frequently enriched with amino acids. These are primarily lysine and methionine. To ensure the mineral and vitamin supply of the farm animals, in addition minerals and vitamins are added. The type and amount of added minerals and vitamins depends on the animal species and is known to those skilled in the art (see, e.g. Jeroch et al., Ernährung landwirtschaftlicher Nutztiere [Nutrition of agricultural farm animals], Ulmer, UTB). To cover the nutrient and energy requirement, use can be made of complete feeds which comprise all nutrients in a ratio to one another covering requirements. It can form the sole feed of the animals. Alternatively, a supplementary feed can be added to a grain feed of cereals. The supplement feed can comprise protein-, mineral- and vitamin-rich feed mixtures which supplement the feed.

The inventively produced solid sodium diformate preparation is suitable, in particular, as what is termed an acidifier. Acidifiers are taken to mean those substances which lower the pH. The expression comprises not only those substances which lower the pH in the substrate (e.g. animal feed), but also those which lower the pH in the gastrointestinal tract of the animal.

The inventively produced solid sodium diformate preparation is suitable in particular as a composition having performance- and/or growth-promoting effect. In a preferred embodiment, the solid sodium diformate preparation is used as such a performance- and/or growth-promoting composition for monogastric animals, in particular for hogs and/or poultry.

The inventively produced solid sodium diformate preparation is suitable, in addition, as preservative, in particular as preservative for green feeds and/or animal feeds.

The inventively produced solid sodium diformate preparation can be used advantageously in the production of silage. It accelerates lactic acid fermentation and/or prevents secondary fermentation and inhibits the development of harmful yeasts, so that they can be used as silage additives (silage aids).

Use of the inventively produced solid sodium diformate preparation as fertilizer is also possible.

DESCRIPTION OF THE FIGURES

FIG. 1 corresponds essentially to FIG. 2 of EP 0 824 511 B1, with the latter, however, not showing the ejected stream (7a). Sodium diformate can only be obtained in this process variant when, in the reaction mixture from which the product is to be crystallized out, the molar ratios of formic acid to sodium formate and to water are set in accordance with the statements made for the inventive process.

In detail, in the process shown in FIG. 1, a procedure is followed such that formic acid is provided as stream (1) and is combined with a sodium formate-comprising stream (10) to produce a stream (2) representing the reaction mixture. The reaction mixture is fed as stream (2) to a crystallization stage and is brought to crystallization, producing a solid phase and a mother liquor. The solid phase and the mother liquor are fed in the form of stream (3) to a separation stage in which the solid phase is separated off from the mother liquor, a stream (4) comprising sodium diformate and a stream (5) comprising the mother liquor being obtained. The stream (5) is fed together with a caustic soda solution stream (6) to a neutralization stage, resulting in a mixture comprising sodium formate. A part of this mixture is taken off as stream (7a). The remaining part is fed as stream (7) to a concentration stage in which a part of the water present in stream (7) is discharged as stream (9). Here, the stream (10) comprising sodium formate is produced, which stream is recirculated to step b).

In detail, in the process depicted in FIG. 2, generally a procedure is followed in such a manner that a stream (1) of formic acid having a formic acid content of at least 74% by weight is prepared. The stream (1) is combined with two streams (5a) and (10) comprising sodium formate to produce a stream (2). The stream (2) is fed to a crystallization stage, with, if appropriate with temperature elevation, the aqueous solution being obtained which has a molar ratio of HCOOH:HCOONa of greater than 1.5:1 and a molar ratio of HCOOH:H$_2$O of at least 1.1:1. The aqueous solution is brought to crystallization, obtaining the solid phase and the mother liquor, e.g. by evaporation and/or temperature reduction. The solid phase and the mother liquor are fed in the form of a stream (3) to a separation stage in which the solid phase is separated off from the mother liquor. The stream (4) comprising sodium diformate is ejected. The stream (5) comprising the mother liquor is divided into two substreams (5a) and (5b). The stream (5a) is recirculated as subquantity (A) to the crystallization stage. The stream (5b) is fed as subquantity (B) together with a stream (6) comprising sodium hydroxide and/or sodium carbonate to a neutralization stage. If appropriate, from the mixture comprising sodium formate resulting from the neutralization a part is taken off in the form of stream (7a). The remaining part is fed as stream (7) to a concentration stage (evaporation) in which a part of the water present in the stream (7) is discharged as stream (9). The resultant stream (10) comprising sodium formate is recirculated to the crystallization stage to which streams (1) and (5a) are also fed.

FIG. 3 shows a diagrammatic representation of a process variant of the inventive process. The stream (5b) is neutralized and concentrated by evaporation. The water content of the resultant sodium formate-containing stream (10) is, before recirculation to the (first) crystallization stage, separately decreased by crystallization and phase separation.

In detail, in the process shown in FIG. 3, a procedure is followed in such a way that a stream (1) of formic acid having a formic acid content of at least 74% by weight is provided. The stream (1) is combined with two streams (5a) and (14) comprising sodium formate to produce a stream (2). The stream (2) is fed to a first crystallization stage, in which case, if appropriate with temperature elevation, the aqueous solution is obtained which has a molar ratio of HCOOH:Na[HCOO] of greater than 1.5:1 and a molar ratio of HCOOH:H$_2$O of at least 1.1:1. The aqueous solution is brought to crystallization, to produce the solid phase and the mother liquor, e.g. by means of evaporation or temperature reduction. The solid phase and the mother liquor are fed in the form of a stream (3) to a first separation stage in which the solid phase is separated off from the mother liquor. The stream (4) comprising sodium diformate is ejected. The stream (5) comprising the mother liquor is divided into two substreams (5a) and (5b). The stream (5a) is recirculated as subquantity (A) to the step b). The stream (5b) is fed as subquantity (B) together with a stream (6) comprising sodium hydroxide and/or sodium carbonate, to a neutralization stage. If appropriate, from the mixture comprising sodium formate resulting from the neutralization a part (not shown) is taken off. The mixture is combined with a stream (13a) comprising sodium formate, obtaining a stream (8). The stream (8) is fed to a concentration stage (evaporation) in which part of the water present in stream (8) is discharged as stream (9). The water content of the resultant sodium formate-comprising stream (10) is, before recirculation to step b), reduced by the following steps. The stream (10) is combined with a stream (13b) comprising sodium formate, to produce a stream (11). The stream (11) is fed to a second crystallization stage in which the stream (11) is brought to crystallization, to produce a second solid phase and a second mother liquor, e.g. by means of evaporation or temperature reduction. The second solid phase and second mother liquor are fed in the form of a stream (12) to a second separation stage in which the second solid phase is separated off from the second mother liquor. This yields a stream (13) comprising the second mother liquor and a stream (14) comprising sodium formate. The sodium formate-comprising stream (14) is recirculated to the first crystallization stage. The stream (13) comprising the mother liquor is divided into two substreams (13a) and (13b). The substream (13a) is combined with the stream (7), to produce the stream (8). Stream (8) is fed to the concentration stage (evaporation). The substream (13b) is combined with the stream (10) to produce the stream (11). The stream (11) is fed to the second crystallization stage. In this process variant it is in addition possible to take off the stream (13) in part and eject it (not shown).

FIG. 4 shows a diagrammatic representation of a variant of the inventive process shown in FIG. 3. In this case also, a second separation stage produces a stream (13) comprising the second mother liquor and a stream (14) comprising sodium formate The stream (14) comprising sodium formate is likewise recirculated to the first crystallization stage. The stream (13) comprising the mother liquor is combined with the stream (7) to produce the stream (8). The stream (8) is fed to the concentration stage (evaporation). In this process variant it is in addition possible to take off the stream (13) in part and eject it (not shown).

FIG. 5 shows a diagrammatic representation of a further variant of the inventive process shown in FIG. 3. In this case also a second separation stage produces a stream (13) comprising the second mother liquor, and a stream (14) comprising sodium formate. The stream (14) comprising sodium formate is likewise recirculated to the first crystallization stage. The stream (13) comprising the mother liquor is combined with the stream (10) to produce the stream (11). The stream (11) is fed to the second crystallization stage. In this process variant it is in addition possible to remove the stream (13) in part and eject it (not shown).

The examples hereinafter serve to illustrate the invention and are not in any way to be taken as limiting.

EXAMPLES

I. Production of Sodium Diformate Preparations without Recirculation of Mother Liquor (Comparative Examples)

The comparative examples I.1 and I.2 were carried out in a 1 l stirred vessel which was equipped with heating and cooling apparatus and also an outlet. The molar ratios of the components in the aqueous solution to be crystallized correspond in each case to the values to be set in the inventive process.

Comparative Example I.1 (According to DE 102005017089.7)

650 g of a 94% strength aqueous formic acid solution were charged and heated with stirring to 55° C. The stirring was continued during the entire experimental period. 350 g of solid sodium formate (purity>97%) were dissolved in the formic acid solution, a clear solution being obtained. The solution was then slowly cooled. After about 4 hours, a temperature of about 12° C. was reached at which a sudden precipitation was observed. The suspension was heated to about 35° C. until only a slight turbidity was observed. The suspension was then cooled to 20° C. over a period of about 6 h and run off from the stirred vessel. The mother liquor was separated off from the crystals by means of a suction filter. The yield of moist sodium diformate preparation was about 125 g. After drying was carried out in the vacuum drying cabinet at a temperature of 35° C., the residual water content in the product was determined at approximately 0.1% by weight, based on the total dry weight of about 122 g. The content of formic acid in the dried product was 40.3% by weight, based on the total dry weight.

Comparative Example I.2 (According to DE 102005017089.7)

650 g of an 80% by weight aqueous formic acid solution were charged and heated to 55° C. with stirring. Under continued stirring, 430 g of solid sodium formate (purity>97%) were dissolved in the formic acid solution, a clear solution being obtained. The solution was then slowly cooled. After about 5 hours, a temperature of about 24° C. was reached, at which a sudden precipitation was observed. The suspension was heated to about 35° C. with stirring, until only a slight turbidity was observed. The suspension was then cooled to 15° C. over a period of about 6 h and run off from the stirred vessel. The mother liquor was separated off from the crystals by means of a suction filter. The yield of moist sodium diformate preparation was about 280 g. After the product was dried in the vacuum drying cabinet at a temperature of 35° C., the residual water content in the product was determined at approximately 0.15% by weight, based on the total dry weight of 270 g. The content of formic acid in the dried product was 40.1% by weight, based on the total dry weight.

Comparative Example I.3 (Similar to Example 2 of DE 424017)

The molar ratios of the components in the aqueous solution to be crystallized do not correspond to the values to be set in the inventive process.

476 g of an 80% strength by weight aqueous formic acid solution were charged. With stirring, 524 g of solid sodium formate were added. For complete dissolution, the mixture was heated to a temperature of 120° C. The solution was then slowly cooled. From about 112° C., crystallization was started. It was cooled further to 25° C. at a rate of about 0.7 K/min. The suspension was then allowed to stand for 24 h with slight stirring. Thereafter, the crystals formed were separated off from the mother liquor. The yield of moist product was about 370 g. The content of formic acid was about 21.8% by weight, based on the total weight of the moist product.

II. Production of Sodium Diformate Preparations with Recirculation of Mother Liquor Comparative Example II.1 (Stream Circuit Similar to EP 0 824 511 B1)

Figure 1:
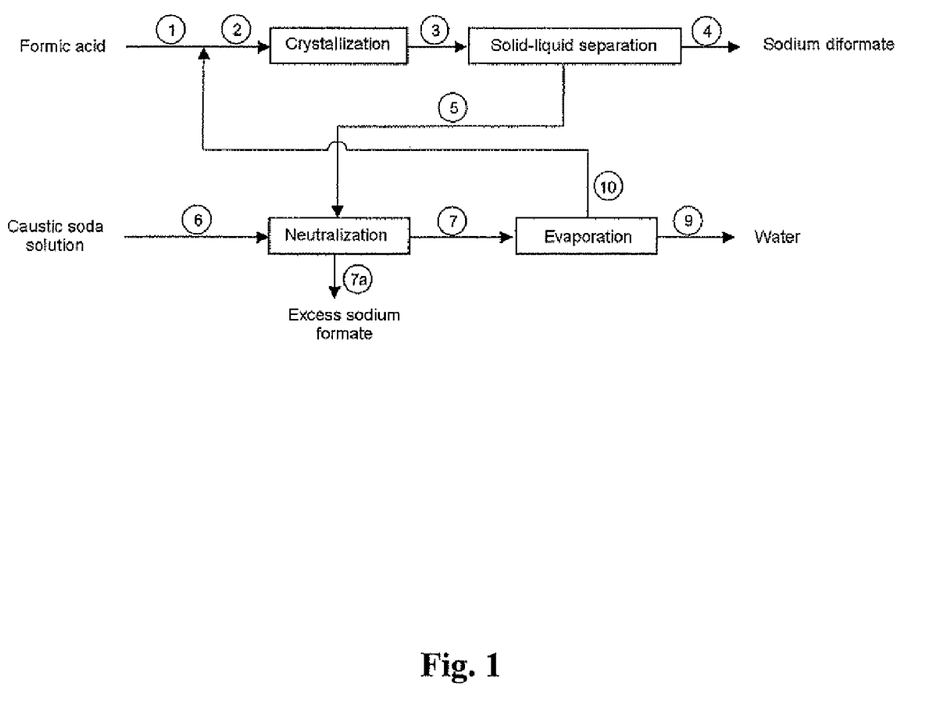
FIG. 1 shows a diagrammatic representation of a process variant of EP 0 824 511 B1, in which the mother liquor, after complete neutralization, is recirculated to the crystallization stage.

Reference is made to the accompanying FIG. 1 which shows a diagrammatic representation of a process variant of EP 0 824 511 B1, in which the mother liquor, after complete neutralization, is recirculated to the crystallization stage. FIG. 1 corresponds essentially to FIG. 2 of EP 0 824 511 B1, the latter, however, not showing the ejected stream (7a).

In the Tables 1a and 1b hereinafter, a balance of the material flows is given which may be prepared on the basis of the statements made in EP 0 824 511 B1 on the stream circuit according to FIG. 2 of EP 0 824 511 B1. In this case, as stream (1), an 85% strength by weight formic acid solution is fed, and as stream (6) a 50% strength aqueous caustic soda solution is fed, as stream (10) an 80% strength by weight sodium formate solution is recirculated to the crystallization stage (crystallization).

In this context, however, reference may be made explicitly to the fact that EP 0 824 511 B1, apart from the abovementioned material flows, gives no further specific data on the material flows to be set. In particular, the molar ratio set in the Examples II.1 and II.2 shown here of formic acid to sodium formate in the stream (2) to be crystallized does not correspond to the molar ratios specified as preferred according to EP 0 824 511 B1, but was set in accordance with the range to be maintained for the inventive process, since only in this manner it is ensured that the resultant stream (4) actually comprises sodium diformate in a form as pure as possible.

TABLE 1a

|  |  | 1 | 2 | 3 | 4 | 5 | 6 | 7 | 7a | 9 | 10 |
|---|---|---|---|---|---|---|---|---|---|---|---|
| t/h | NaFo * FA(s) |  |  |  | 1 | 1 |  |  |  |  |  |
|  | NaFo |  | 1.41 | 0.81 | 0.03 | 0.78 |  | 1.38 | 1.56 |  | 1.38 |
|  | FA | 1.86 | 1.92 | 1.52 | 0.06 | 1.46 |  |  |  |  |  |
|  | H₂O | 0.33 | 0.67 | 0.67 | 0.02 | 0.65 | 1.27 | 1.17 | 1.32 | 0.82 | 0.34 |
|  | NaOH |  |  |  |  |  | 1.27 |  |  |  |  |
|  | Total | 2.19 | 4.00 | 4.00 | 1.11 | 2.89 | 2.54 | 2.54 | 2.88 |  | 1.72 |
| Solution % by weight | NaFo |  | 35.17 | 27.01 |  | 27.01 |  | 54.14 | 54.14 |  | 80.00 |
|  | FA | 85.00 | 48.00 | 50.55 |  | 50.55 |  |  |  |  |  |
|  | H₂O | 15.00 | 16.83 | 22.44 |  | 22.44 | 50.00 | 45.86 | 45.86 |  | 20.00 |
|  | NaOH |  |  |  |  |  | 50.00 |  |  |  |  |

TABLE 1b

|  |  | 1 | 2 | 3 | 4 | 5 | 6 | 7 | 7a | 9 | 10 |
|---|---|---|---|---|---|---|---|---|---|---|---|
| kmol/h | NaFo * FA(s) |  |  |  | 1 | 1 |  |  |  |  |  |
|  | NaFo |  | 2.36 | 1.36 | 0.05 | 1.31 |  | 2.31 | 2.62 |  | 2.31 |
|  | FA | 4.62 | 4.76 | 3.76 | 0.14 | 3.62 |  |  |  |  |  |
|  | H₂O | 2.08 | 4.26 | 4.26 | 0.16 | 4.10 | 8.04 | 7.38 | 8.38 | 5.21 | 2.18 |
|  | NaOH |  |  |  |  |  | 3.62 |  |  |  |  |
|  | Total | 6.70 | 11.38 | 10.38 | 1.35 | 9.03 | 11.66 | 9.69 | 10.99 | 5.21 | 4.49 |
| Solution mol % | NaFo |  | 20.73 | 14.48 | 14.48 | 14.48 |  | 23.81 | 23.81 |  | 51.43 |
|  | FA | 68.92 | 41.81 | 40.07 | 40.07 | 40.07 |  |  |  |  |  |
|  | H₂O | 31.08 | 37.46 | 45.45 | 45.45 | 45.45 | 68.97 | 76.19 | 76.19 | 100.0 | 48.57 |
|  | NaOH |  |  |  |  |  | 31.03 |  |  |  |  |

In the Tables 1a and 1b, NaFo*FA(s) is solid sodium diformate, NaFo is sodium formate, FA is formic acid, H₂O is water, NaOH is sodium hydroxide; the numbers 1 to 10 in the first lines of each table designate the stream denoted by the respective number in FIG. 1; solution % by weight designates the parts by weight of the components in the respective liquid part of the stream (ie without solid fractions), solution mol % the corresponding molar fractions.

The calculation of the above balance shows that the weight ratios used here of the components in streams (1) and (10) can only be set when a considerable part, that is to say more than 50% by weight, of the sodium formate solution produced in the neutralization stage is ejected as stream (7a). Furthermore, on combination of the streams (1) and (10), a stream (2) is produced which has a water content of more than 16% by weight and thus has a crystallization temperature of below 20° C.

Comparative Example II.2
(Similar to EP 0 824 511 B1)

For the Comparative Example II.2, likewise reference is made to the accompanying FIG. 1. As stream (1), a 94% strength by weight formic acid solution is fed, and as a stream (6), a 50% strength by weight aqueous caustic soda solution is fed, as stream (10), an 80% strength by weight sodium formate solution is recirculated to the crystallization stage (crystallization). The remainder of the procedure is carried out in accordance with Comparative Example II.1. The Tables 2a and 2b hereinafter give the balance of the material flows calculated in this case.

Calculation of the above balance shows that the weight ratios used here of the components in streams (1) and (10) can only be set when a considerable part, that is to say about 46% by weight, of the sodium formate solution produced in the neutralization stage is ejected as stream (7a).

Example II.1

Reference is made to the accompanying FIG. 2 which shows a diagrammatic representation of a process variant of the inventive process in which the mother liquor is divided into two substreams (5a) and (5b). The stream (5a) is recirculated directly to the crystallization stage, the stream (5b) not until after complete neutralization by the stream (6).

Tables 3a and 3b hereinafter show the balance of the material flows calculated in this case. As stream (1), a 94% strength by weight formic acid solution is fed, and as stream (6), a 50% strength by weight aqueous caustic soda solution. The division of the stream (5) into the substreams (5a) and (5b) is chosen in such a manner that the weight ratio of stream (5a) to stream (5b) is about 2.4:1, and the molar ratio of formic acid in the stream (5b) to the total amount of sodium diformate and sodium formate in the stream (4) is as far as possible 1:1. In this case, as stream (10), an 85% strength by weight solution or suspension of sodium formate is recirculated to the crystallization stage (crystallization).

TABLE 2a

| | | 1 | 2 | 3 | 4 | 5 | 6 | 7 | 7a | 9 | 10 |
|---|---|---|---|---|---|---|---|---|---|---|---|
| t/h | NaFo * FA(s) | | | 1 | 1 | | | | | | |
| | NaFo | | 1.31 | 0.72 | 0.03 | 0.68 | | 1.28 | 1.09 | | 1.28 |
| | FA | 1.54 | 1.60 | 1.20 | 0.06 | 1.14 | | | | | |
| | H₂O | 0.10 | 0.42 | 0.42 | 0.02 | 0.40 | 0.99 | 0.99 | 0.84 | 0.67 | 0.32 |
| | NaOH | | | | | | 0.99 | | | | |
| | Total | 1.64 | 3.33 | 3.33 | 1.11 | 2.22 | 1.98 | 2.27 | 1.93 | | 1.60 |
| Solution % by weight | NaFo | | 39.44 | 30.78 | | 30.78 | | 56.34 | 56.34 | | 80.00 |
| | FA | 94.00 | 48.00 | 51.28 | | 51.28 | | | | | |
| | H₂O | 6.00 | 12.56 | 17.94 | | 17.94 | 50.00 | 43.66 | 43.66 | | 20.00 |
| | NaOH | | | | | | 50.00 | | | | |

TABLE 2b

| | | 1 | 2 | 3 | 4 | 5 | 6 | 7 | 7a | 9 | 10 |
|---|---|---|---|---|---|---|---|---|---|---|---|
| kmol/h | NaFo * FA(s) | | | 1 | 1 | | | | | | |
| | NaFo | | 2.20 | 1.20 | 0.06 | 1.15 | | 2.15 | 1.82 | | 2.15 |
| | FA | 3.82 | 3.96 | 2.96 | 0.14 | 2.82 | | | | | |
| | H₂O | 0.64 | 2.65 | 2.65 | 0.13 | 2.52 | 6.27 | 6.28 | 5.34 | 4.26 | 2.03 |
| | NaOH | | | | | | 2.82 | | | | |
| | Total | 4.45 | 8.82 | 7.82 | 1.32 | 6.50 | 9.10 | 8.43 | 7.16 | 4.26 | 4.17 |
| Solution mol % | NaFo | | 24.99 | 17.65 | 17.65 | 17.65 | | 25.46 | 25.46 | | 51.43 |
| | FA | 85.98 | 44.95 | 43.47 | 43.47 | 43.47 | | | | | |
| | H₂O | 14.02 | 30.06 | 38.87 | 38.87 | 38.87 | 68.97 | 75.54 | 75.54 | 100.0 | 48.57 |
| | NaOH | | | | | | 31.03 | | | | |

TABLE 3a

|  |  | 1 | 2 | 3 | 4 | 5 | 5a | 5b | 6 | 7 | 7a | 9 | 10 |
|---|---|---|---|---|---|---|---|---|---|---|---|---|---|
| t/h | NaFo * FA(s) |  |  | 1.00 | 1.00 |  |  |  |  |  |  |  |  |
|  | NaFo |  | 1.42 | 0.83 | 0.03 | 0.80 | 0.56 | 0.23 |  | 0.86 |  |  | 0.86 |
|  | FA | 0.88 | 1.92 | 1.52 | 0.06 | 1.46 | 1.04 | 0.42 |  |  |  |  |  |
|  | $H_2O$ | 0.06 | 0.66 | 0.66 | 0.02 | 0.63 | 0.45 | 0.18 | 0.37 | 0.72 |  | 0.57 | 0.15 |
|  | NaOH |  |  |  |  |  |  |  | 0.37 |  |  |  |  |
|  | Total | 0.94 | 4.00 | 4.00 | 1.11 | 2.89 | 2.05 | 0.84 | 0.74 | 1.58 | 0.00 | 0.57 | 1.01 |
| Solution | NaFo |  | 35.59 | 27.57 | 27.57 | 27.57 | 27.57 | 27.57 |  | 54.44 |  |  | 85.0 |
| % by | FA | 94.00 | 48.00 | 50.55 | 50.55 | 50.55 | 50.55 | 50.55 |  |  |  |  |  |
| weight | $H_2O$ | 6.00 | 16.41 | 21.88 | 21.88 | 21.88 | 21.88 | 21.88 | 50.00 | 45.56 |  | 100.0 | 15.0 |
|  | NaOH |  |  |  |  |  |  |  | 50.00 |  |  |  |  |

TABLE 3b

|  |  | 1 | 2 | 3 | 4 | 5 | 5a | 5b | 6 | 7 | 7a | 9 | 10 |
|---|---|---|---|---|---|---|---|---|---|---|---|---|---|
| kmol/h | NaFo * FA(s) |  |  | 1 | 1 |  |  |  |  |  |  |  |  |
|  | NaFo |  | 2.39 | 1.39 | 0.05 | 1.33 | 0.95 | 0.39 |  | 1.44 |  |  | 1.44 |
|  | FA | 2.19 | 4.76 | 3.76 | 0.14 | 3.62 | 2.57 | 1.05 |  |  |  |  |  |
|  | $H_2O$ | 0.36 | 4.15 | 4.15 | 0.15 | 4.00 | 2.84 | 1.16 | 2.34 | 4.55 |  | 3.59 | 0.96 |
|  | NaOH |  |  |  |  |  |  |  | 1.05 |  |  |  |  |
|  | Total | 2.55 | 11.30 | 10.30 | 1.34 | 8.95 | 6.35 | 2.60 | 3.39 | 5.99 | 0.00 | 3.59 | 2.40 |
| Solution | NaFo |  | 21.12 | 14.91 | 14.91 | 14.91 | 14.91 | 14.91 |  | 24.03 |  |  | 60.00 |
| mol % | FA | 85.98 | 42.10 | 40.40 | 40.40 | 40.40 | 40.40 | 40.40 |  |  |  |  |  |
|  | $H_2O$ | 14.02 | 36.78 | 44.69 | 44.69 | 44.69 | 44.69 | 44.69 | 68.97 | 75.97 |  | 100.0 | 40.00 |
|  | NaOH |  |  |  |  |  |  |  | 31.03 |  |  |  |  |

The calculation of the above balance shows that the division of the stream (5) into the streams (5a) and (5b) used here leads to the fact that in the neutralization stage no excess sodium formate is produced, so that any ejection via stream (7a) can be omitted.

Example II.2

Reference is made to the accompanying FIG. 3 which shows a diagrammatic representation of a process variant of the inventive process in which the mother liquor is divided into two substreams (5a) and (5b). The stream (5a) is recirculated directly to the (first) crystallization stage. The stream (5b) is completely neutralized by the stream (6) and evaporated. The resultant stream (10) comprising sodium formate is (in the second crystallization stage) brought to crystallization; the resultant liquid phase is fed as stream (13) together with stream (7) to the evaporation stage; the solid phase comprising sodium formate is fed, as stream (14), together with the streams (1) and (5a) to the (first) crystallization stage.

The Tables 4a and 4b hereinafter show the balance of the material flows calculated in this case. As stream (1), a 94% strength by weight formic acid solution is fed, and as stream (6) a 50% strength by weight aqueous caustic soda solution is fed. The division of the stream (5) into substreams (5a) and (5b) is chosen in such a manner that the weight ratio of stream (5a) to stream (5b) is about 2:1 and the molar ratio of formic acid in the stream (5b) to the total amount of sodium diformate and sodium formate in stream (4) is as far as possible 1:1. In this case, sodium formate is recirculated in the form of the stream (14) essentially as solid having a low fraction of residual moisture to the (first) crystallization stage.

TABLE 4a

|  |  | 1 | 2 | 3 | 4 | 5 | 5a | 5b | 6 | 7 | 8 | 9 | 10 | 11 | 12 | 13 | 13a | 13b | 14 |
|---|---|---|---|---|---|---|---|---|---|---|---|---|---|---|---|---|---|---|---|
| t/h | NaFo * FA(s) |  |  | 1.00 | 1.00 |  |  |  |  |  |  |  |  |  |  |  |  |  |  |
|  | NaFo(s) |  |  |  |  |  |  |  |  |  |  |  |  |  | 0.80 |  |  |  | 0.80 |
|  | NaFo |  | 1.29 | 0.69 | 0.03 | 0.66 | 0.44 | 0.22 |  | 0.84 | 2.39 |  | 2.39 | 2.39 | 1.59 | 1.54 | 1.54 |  | 0.04 |
|  | FA | 0.89 | 1.77 | 1.36 | 0.06 | 1.30 | 0.87 | 0.43 |  |  |  |  |  |  |  |  |  |  |  |
|  | $H_2O$ | 0.06 | 0.28 | 0.28 | 0.01 | 0.27 | 0.18 | 0.09 | 0.37 | 0.62 | 2.04 | 0.58 | 1.46 | 1.46 | 1.46 | 1.42 | 1.42 |  | 0.04 |
|  | NaOH |  |  |  |  |  |  |  | 0.37 |  |  |  |  |  |  |  |  |  |  |
|  | Total | 0.95 | 3.33 | 3.33 | 1.11 | 2.22 | 1.49 | 0.73 | 0.74 | 1.47 | 4.43 | 0.58 | 3.85 | 3.85 | 3.85 | 2.96 | 2.96 | 0.00 | 0.89 |
| Solution | NaFo |  | 38.59 | 29.55 | 29.55 | 29.55 | 29.55 | 29.55 |  | 57.50 |  |  | 62.00 | 62.00 |  | 50.60 | 50.60 |  | 50.60 |
| % by | FA | 94.00 | 53.00 | 58.43 | 58.43 | 58.43 | 58.43 | 58.43 |  |  |  |  |  |  |  |  |  |  |  |
| weight | $H_2O$ | 6.00 | 8.41 | 12.02 | 12.02 | 12.02 | 12.02 | 12.02 | 50.00 | 42.50 |  |  | 38.00 | 38.00 |  | 49.40 | 49.40 |  | 49.40 |
|  | NaOH |  |  |  |  |  |  |  | 50.00 |  |  |  |  |  |  |  |  |  |  |

TABLE 4b

|   |   | 1 | 2 | 3 | 4 | 5 | 5a | 5b | 6 | 7 | 8 | 9 | 10 | 11 | 12 | 13 | 13a | 13b | 14 |
|---|---|---|---|---|---|---|----|----|---|---|---|---|----|----|----|----|-----|-----|----|
| kmol/h | NaFo * |  |  | 1.00 | 1.00 |  |  |  |  |  |  |  |  |  |  |  |  |  |  |
|  | FA(s) |  |  |  |  |  |  |  |  |  |  |  |  |  |  |  |  |  |  |
|  | NaFo(s) |  |  |  |  |  |  |  |  |  |  |  |  |  | 1.34 |  |  |  | 1.34 |
|  | NaFo |  | 2.15 | 1.15 | 0.06 | 1.10 | 0.74 | 0.36 |  | 1.42 | 4.00 |  | 4.00 | 4.00 | 2.66 | 2.59 | 2.59 |  | 0.08 |
|  | FA | 2.22 | 4.38 | 3.38 | 0.16 | 3.21 | 2.16 | 1.06 |  |  |  |  |  |  |  |  |  |  |  |
|  | H$_2$O | 0.36 | 1.77 | 1.77 | 0.08 | 1.69 | 1.14 | 0.55 | 2.34 | 3.95 | 12.94 | 3.66 | 9.27 | 9.27 | 9.27 | 8.99 | 8.99 |  | 0.28 |
|  | NaOH |  |  |  |  |  |  |  | 1.06 |  |  |  |  |  |  |  |  |  |  |
|  | Total | 2.58 | 8.30 | 7.30 | 1.30 | 6.00 | 4.03 | 1.97 | 3.40 | 5.37 | 16.94 | 3.66 | 13.27 | 13.27 | 13.27 | 11.57 | 11.57 | 0.00 | 1.69 |
| Solution mol % | NaFo |  | 25.95 | 18.32 | 18.32 | 18.32 | 18.32 | 18.32 |  | 26.37 | 23.62 |  | 30.16 | 30.16 | 22.31 | 22.34 | 22.34 |  | 21.33 |
|  | FA | 85.98 | 52.68 | 53.53 | 53.53 | 53.53 | 53.53 | 53.53 |  |  |  |  |  |  |  |  |  |  |  |
|  | H$_2$O | 14.02 | 21.37 | 28.15 | 28.15 | 28.15 | 28.15 | 28.15 | 68.97 | 73.63 | 76.38 | 100.00 | 69.84 | 69.84 | 77.69 | 77.66 | 77.66 |  | 78.67 |
|  | NaOH |  |  |  |  |  |  |  | 31.03 |  |  |  |  |  |  |  |  |  |  |

The invention claimed is:

1. A process for producing a solid sodium diformate preparation having a formic acid content of at least 35% by weight, based on the total weight of the sodium diformate preparation, wherein
an aqueous solution is produced at an elevated temperature from sodium formate and at least 74% strength by weight formic acid, the aqueous solution having a molar ratio of HCOOH:HCOONa of greater than 1.5:1 and a molar ratio of HCOOH:H$_2$O of at least 1.1:1,
the aqueous solution is brought to crystallization, and the solid sodium diformate preparation is separated off from the mother liquor,
(i) a subquantity (A) of the mother liquor being recirculated for the production of the aqueous solution and
(ii) a subquantity (B) of the mother liquor being admixed with a sodium-containing base and the resultant mixture comprising sodium formate, if appropriate after ejecting a part of same, and if appropriate alter concentrating same, likewise being recirculated for the production of the aqueous solution;
and the subquantities (A) and (B) of the mother liquor totaling 100% by weight of the mother liquor.

2. The process according to claim 1, wherein the aqueous solution is produced at a temperature of not above 100° C.

3. The process according to claim 1, wherein the weight ratio of subquantity (A) to subquantity (B) of the mother liquor is in the range from 20:1 to 1:10.

4. The process according to claim 1, wherein the ratio of subquantity (A) to subquantity (B) of the mother liquor is set in such a manner that the molar ratio of HCOOH in the subquantity (B) of the mother liquor to the total amount of substance of the sodium diformate present in the resultant solid phase, and if appropriate sodium formate present, before a subsequent drying of the solid phase, if appropriate, is at most 1.2:1.

5. The process according to claim 1, wherein the base comprising sodium in step (ii) is selected from sodium hydroxide, sodium carbonate, sodium hydrogencarbonate, sodium C$_1$-C$_6$-alkanolates and mixtures thereof.

6. The process according to claim 1, wherein, in step (ii), the subquantity (B) of the mother liquor is essentially completely neutralized.

7. The process according to claim 1, wherein, in step (ii), at most 20% by weight of the mixture comprising sodium formate is taken off, based on the total weight of the mixture comprising sodium formate.

8. The process according to claim 1, wherein, of the mixture comprising sodium formate obtained in step (ii), a part is taken off and ejected, wherein the amount of sodium formate present in the remaining part of the mixture together with the amount of sodium formate present in the subquantity (A) of the mother liquor gives the total amount of sodium formate used for producing the aqueous solution.

9. The process according to claim 1, wherein the water content of the mixture comprising sodium formate from step (ii), before its use in the production of the aqueous solution, is decreased to at most 20% by weight, based on the total weight of the mixture.

10. The process according to claim 9, wherein the water content is decreased by means of an evaporation stage, or, by means of a second crystallization stage in which a second solid phase and a second mother liquor are obtained, and a second concentration stage in which the second solid phase is separated off from the second mother liquor.

11. The process according to claim 1, in which
a) a stream (1) of formic acid having a formic acid content of at least 74% by weight is prepared;
b) the stream (1) from step a) having two streams (5a) and (10) comprising the sodium formate is fed to a crystallization stage, wherein, if appropriate with temperature elevation, the aqueous solution which has a molar ratio of HCOOH:HCOONa of greater than 1.5:1 and a molar ratio of HCOOH:H$_2$O of at least 1.1:1 is produced;
c) in the crystallization stage the aqueous solution from step b) is brought to crystallization to produce a stream (3) having the solid phase and the mother liquor;
d) the stream (3) from step c) is fed to a separation stage in which the solid phase is separated off from the mother liquor, a stream (4) comprising the sodium diformate and a stream (5) comprising the mother liquor being produced;
e) the stream (5) from step d) is divided into two substreams (5a) and (5b);
f) the stream (5a) from step e) is recirculated as subquantity (A) to step b);
g) the stream (5b) from step e) is fed to a neutralization stage as subquantity (B) together with a stream (6) comprising the sodium-containing base, resulting in the mixture comprising sodium formate; and
h) the mixture from step g) comprising sodium formate, if appropriate after taking off a part of same in the form of stream (7a), is fed as stream (7) to a concentration stage in which a part of the water present in the stream (7) is discharged as stream (9), the stream (10) comprising sodium formate being produced, which is recirculated to the step b).

12. The process according to claim 11, wherein in step d) the stream (5) essentially comprises formic acid in the range from 35 to 80% by weight, sodium formate in the range from 20 to 45% by weight, and water in the range from 0 to 30% by weight, in each case based on the total weight of the stream (5).

13. The process according to claim 11, wherein, in step g), as stream (6), an aqueous caustic soda solution having an NaOH content in the range from 10 to 60% by weight, based on the total weight of the aqueous caustic soda solution, is used.

14. The process according to claim 11, wherein the stream (10) from step h) essentially comprises sodium formate in the range form 50 to 100% by weight and water in the range from 0 to 50% by weight, in each case based on the total weight of the stream (10).

15. The process according to claim 11, in which, in addition, k) the sodium formate-comprising stream (10) from step h), before it is recirculated to step b) is fed to a second crystallization stage and is brought herein to crystallization, producing a second solid phase and a second mother liquor;

l) the second solid phase and second mother liquor obtained from step k) is fed in the form of a stream (12) to a separation stage in which the second solid phase is separated off from the second mother liquor, producing a stream (13) comprising the second mother liquor and a stream (14) comprising sodium formate;

m) the sodium formate-comprising stream (14) from step l) is recirculated to the step b) and used herein as stream (10); and n) the mother liquor-comprising stream (13) from step l)

n1) is recirculated to the step h) and herein is fed together with the stream (7) to the concentration stage of the step h);

n2) is recirculated to the step k) and herein is fed together with the stream (10) to the second crystallization stage;

n3) is divided into the substreams (13*a*) and (13*b*), the substream (13*a*) is recirculated to the step h) and herein is fed together with the stream (7) to the concentration stage of the step h) and the substream (13*b*) is recirculated to the step k) and herein is fed together with the stream (10) to the second crystallization stage; and/or n4) is in part taken off and ejected.

16. The process according to claim 15, wherein the stream (13) from step l) comprising the mother liquor essentially comprises water in the range from 20 to 50% by weight and sodium formate in the range from 50 to 80% by weight, in each case based on the total weight of the stream (13).

17. The process according to claim 15, wherein, in step n4), at most 30% by weight of the stream (13), based on the total weight of the stream (13), is taken off and ejected.

18. The process according to claim 15, wherein the stream (13) from step l) comprising the mother liquor is recirculated according to step n1) to step h) and herein fed together with the stream (7) to the concentration stage.

19. The process according to claim 15, wherein the stream (14) from step l) comprising sodium formate essentially comprises sodium formate in the range from 75 to 100% by weight and water in the range from 0 to 25% by weight, in each case based on the total weight of the stream (14).

20. The process according to claim 1, wherein the solid sodium diformate preparation has a formic acid content in the range from 38 to 41% by weight, based on the total weight of the sodium diformate preparation.

21. The process according to claim 1, wherein the solid sodium diformate preparation has a water content of no greater than 0.5% by weight, based on the total weight of the preparation.

* * * * *